United States Patent [19]

Krchnak et al.

[11] Patent Number: 4,833,072

[45] Date of Patent: May 23, 1989

[54] ANTIGENTIC PEPTIDES AND PROCESS FOR THEIR PREPARATION

[75] Inventors: Viktor Krchnak; Milan Krojidlo; Otakar Mach, all of Prague, Czechoslovakia

[73] Assignee: Spofa spojene podniky pro, Prague, Czechoslovakia

[21] Appl. No.: 929,703

[22] Filed: Nov. 13, 1986

[30] Foreign Application Priority Data

Nov. 16, 1985 [CS] Czechoslovakia ............ 8286-85

[51] Int. Cl.$^4$ .................. C12Q 1/70; C07K 7/06; C07K 7/08; C07K 17/08
[52] U.S. Cl. ............................ 435/5; 435/7; 435/805; 435/810; 530/327; 530/328; 422/61
[58] Field of Search ........... 435/5, 7; 530/327, 328; 422/61

[56] References Cited

U.S. PATENT DOCUMENTS 4,629,783  12/1986  Cosand ...................... 530/324

OTHER PUBLICATIONS

Pauletti et al., "Application of a Modified Computor Algorithm in Determining Potential Antigenic Determinants Associated with the AIDS Virus Glycoprotein", Analytical Biochemistry 151, (Dec. 1985), 540–546.
Hattori et al., "Identification of Gag and Enu Gene Products of Human T-Cell Leukenia Virus", Virology, 136(1984), 338–347.
Ratner et al., "Complete Nucleotide Sequence of the AIDS Virus, HTLV-III", Nature, 313(24 Jan. 1985), 277–284.
Dowkenko et al., "Bacterial Expression of the Acquired Immunodificiency Syndrome Retrovirus, p. 24 Gag Protein and Its Use as a Diagnostic Reagent", Proc. Nat'l Acad. Sci. USA 82 (Nov. 1985), 7748–7752.
Steimer et al., "Recombinant Polypeptide from the Endonuclease Region of the Acquired Immune Deficiency Syndrome Retrovirus Polymerase (pol) Gene Detects Serum Antibodies in Most Infected Individuals", J. Virol. 58(Apr. 1986), 9–16.
Montagnier et al., "Identification and Antigenicity of the Major Envelope Glycoprotein of Lymphadenopathy Associated Virus", Virology 144(1985), 283–289.
Muesing et al., "Nucleic Acid Structure and Expression of the Human AIDS/Lymphadenopathy Retrovirus", Nature, 313(7 Feb. 1985), 450–458.
Weigent et al., "The HTLV-III Envelope Protein Contains a Hexapeptide Homologous to a Region of Interleuken-2 that Binds to the Interleukin-2 Receptor", Biochem Biophys. Res. Comm. 139(29 Aug. 1986), 367–374.
Arya et al., "Three Novel Genes of Human T-Lymphotropic Virus Type III: Immune Reactivity of their Products with Sera from Acquired Immune Deficiency Syndrome Patients", Proc. Nat'l. Acad. Sci. USA 83 (4/86), 220 9–2213.

Primary Examiner—Christine M. Nucker
Attorney, Agent, or Firm—Klein & Vibber

[57] ABSTRACT

The present invention relates to antigenic peptides of the formula

H—Val—X—Y             FORMULA I wherein X is a polypeptide residue selected from the group consisting of:
  Val-Pro-Arg-Arg-Lys-Ala-Lys-Ile;
  Ser-Gly-Lys-Ala-Arg-Gly-Trp-Phe;
  Tyr-Tyr-Arg-Asp-Ser-Arg-Ash-Pro-Leu;
  Phe-Ile-His-Asn-Phe-Lys-Arg-Lys-Gly;
  Ser-Ile-Glu-Trp-Arg-Lys-Lys-Arg-Tyr-Ser; and
  Leu-His-Thr-Gly-Glu-Arg-Asp-Trp-His-Leu-Gly, and Y is a hydroxyl group or an amino group. The invention also relates to a method of preparing these peptides.

These novel peptides exhibit useful antigenic properties, with respect to Human Immunodeficiency Virus (HIV), formerly known as Human T-cell Lymphotropic Type-III Virus (HTLV-III). Human Immunodeficiency Virus is associated with the diseases known as Acquired Immune Deficiency Syndrome (AIDS) and Aids Related Complex (ARC). The present antigenic peptides are useful for the detection of antibodies active against HIV and are suitable for use as diagnostic agents. The antigenic peptides of the invention have been shown to induce an in vivo immune response in animals, and the in vitro production of monoclonal antibodies.

13 Claims, No Drawings

ANTIGENTIC PEPTIDES AND PROCESS FOR THEIR PREPARATION

The present invention relates to antigenic peptides that react with antibodies to human immunodeficiency virus (HIV) and can induce the formation of specific antibodies, such peptides having the formula H-Val-X-Y            FORMULA I wherein X is a peptide residue selected from the group consisting of:
Val-Pro-Arg-Arg-Lys-Ala-Lys-Ile;
Ser-Gly-Lys-Ala-Arg-Gly-Trp-Phe;
Tyr-Tyr-Arg-Asp-Ser-Arg-Asn-Pro-Leu;
Phe-Ile-His-Asn-Phe-Lys-Arg-Lys-Gly;
Ser-Ile-Glu-Trp-Arg-Lys-Lys-Arg-Tyr-Ser; and
Leu-His-Thr-Gly-Glu-Arg-Asp-Trp-His-Leu-Gly,
and Y is a hydroxyl group or an amino group. The invention also relates to a method of preparing these peptides.

These novel peptides exhibit useful antigenic properties, with respect to Human Immunodeficiency Virus (HIV), formerly known as Human T-cell Lymphotropic Type-III Virus (HTLV-III). Human Immunodeficiency Virus is associated with the diseases known as Acquired Immune Deficiency Syndrome (AIDS) and Aids Related Complex (ARC). The present antigenic peptides are useful for the detection of antibodies active against HIV and are suitable for use as diagnostic agents. The peptides are also useful for the in vivo production of monodeterminant antibodies.

BACKGROUND OF THE INVENTION

Exposure to HIV and potential susceptibility to the immunodeficiency syndrome can be determined by presence of HIV-antagonizing antibodies in the blood serum of patients. A known assay for the presence of antibodies is the enzyme-linked immunosorbent assay (ELISA), which is based on an interaction between the patient's blood serum and the HIV antigen. According to the ELISA method, the inactivated virus is used as the antigen. The virus is inactivated with tensides (detergents and highly concentrated salt). ELISA microplates coated with this inactivated virus are the main component of the AIDS diagnostic tests kits produced commercially. See, Gallo et al., U.S. Pat. No. 4,520,113; Abbott Laboratories; Inst. Pasteur; Burroughs Wellcome; and others.

A major disadvantage of the ELISA test is that the inactivated virus is nonetheless considered potentially infectious. Producers of the test strictly require that the antigen (virus-coated) plates be handled as a dangerous material. Another disadvantage of the known technique resides in the fact that the virus is not readily available and is difficult to obtain in quantity for preparation of the antigen composition. The virus can be obtained only by a complex multistage technique. First, host cells must be inoculated with the virus in order to produce an infected tissue culture. The virus must then be isolated from the culture medium and purified by several successive operations, before the biological material can be used for the preparation of coated plates according to the ELISA method. This entire procedure is extremely laborious and expensive, and moreover requires the use of an extremely hazardous substrate: a virulent and contagious pathogen.

Another disadvantage of the ELISA method resides in the small but notable probability that any given test will result in a false positive response. Residual contaminants from the original tissue culture are virtually unavoidable, despite thorough purification, and some false positives are therefore inevitable. In view of the reported incidence of non-negligible falsely positive results, all positive results must be verified and confirmed by performing additional tests according to one or more different techniques, such as immunofluorescence assay or the so-called Western blot method.

These disadvantages can be eliminated or substantially diminished by the antigenic polypeptides of the invention.

DESCRIPTION OF THE INVENTION

According to the invention, synthetic oligopeptides which mimic the antigenic properties of HIV can be used as antigens, instead of the known but potentially dangerous viral antigen. This has been achieved by studying the primary nucleotide sequences of various known HIV isolates. See, M. A. Muesing et al., "Nucleic Acid structure and expression of the human AIDS/lymphadenopathy retrovirus," *Nature*, v. 313, pp. 450-8 (1985); S. Wain-Hobson et al., "Nucleotide Sequence of the AIDS Virus, LAV," *Cell*, v. 40, pp. 9-17 (1985); and R. Sanchez-Pescador, et al., "Nucleotide Sequence and Expression of an AIDS-Associated Retrovirus (ARV-2)," *Science*, v. 227, pp. 484-92 (1985). The most virus-specific and conservative regions of the individual viral genes were identified. On the basis of hydrophobicity profiles and correlations, those partial sequences or domains corresponding to protein sequences most likely to carry antigenic properties specific to HIV were selected. All of the antigenic structural fragments or sequences, called epitopes, have a common feature: each fragment begins with the amino acid valine.

The corresponding antigenic oligopeptides, each beginning with valine, were synthesized by fragment synthesis or by successive condensation of the amino acid residues. A preferable method is the Merrifield solid-phase technique, wherein the appropriately protected carboxy terminal amino acid in the sequence is attached to reactive groups of a modified polystyrene-type carrier resin, followed by synthesis of the required peptide chain by a series of successive reaction cycles using protected amino acids and conventional condensing agents. The resulting peptidyl resin is acidolytically cleaved, during which the synthesized peptide chain is detached from the carrier resin and the protecting group is removed.

In a preferred embodiment, polystyrene crosslinked with one percent by weight of divinylbenzene and modified by incorporation of chloromethyl or benzhydrylamine moieties is used as the resin carrier. The N-alpha amino groups of the amino acids are protected by t-butyloxycarbonyl groups, or other acidically removable protecting groups. Acidolytic cleavage and removal of the protecting groups is achieved by treatment with a solution of trifluoroacetic acid in dichloromethane. Side functional groups (usually hydroxyl or amino groups) of bifunctional and multifunctional amino acids are protected with benzyl or related groups, such as benzyloxycarbonyl. The successive condensations of protected amino acids were achieved by the use of suitable reactive derivatives of acids, preferably symmetric anhydrides or N-hydroxybenzotriazol esters.

After synthesis of the peptide chain, the chain is acidically cleaved from the resin carrier with simultaneous removal of the protecting groups from the bifunctional and multifunctional amino acid residues. Cleavage is conveniently performed under the action of liquid hydrogen fluoride or trifluoromethanesulfonic acid in the presence of trifluoroacetic acid and thioanisole.

The crude products obtained from this reaction procedure are purified either by conventional column chromatography, preferably using silica gel provided with a hydrophobic aliphatic hydrocarbon coating, or on molecular sieve carriers. High-performance liquid chromatography (HPLC) is especially preferred. The composition of the resulting peptides can be confirmed by amino acid analysis, and purity can be verified by conventional chromatography and electrophoresis.

The peptides were tested for their specific reactivity with HIV antibodies obtained from sera-positive patients. See, e.g., R. C. Kennedy et al., "Antiserum to a Synthetic Peptide Recognizes the HTLV-III Envelope Glycoprotein," *Science*, v. 231, pp. 1556–9 (1986). The peptides were also used to raise monodeterminant or monoclonal antibodies in rabbits and mice.

The presence of HIV antibodies in the test sera was confirmed by the use of commercially available ELISA sets. The specific reactivity of the peptidic epitopes against the antibodies derived from the proteins coded by different viral genes was determined by the Western blot technique. The peptides were tested for their specific reactivity with HIV antibodies obtained from sera-positive patients. ELISA microplates were coated with the mixture of oligopeptides derived from the different viral proteins, to obtain a representative pattern of specific viral sequences coded by individual viral genes. The coating procedure was carried out to guarantee the appropriate spatial orientation of the oligopeptide molecules and ensure that the antigen-antibody reaction is highly sensitive.

Synthetic ELISA microplates were prepared, using the synthetic oligopeptides to detect HIV antibodies. The test is performed in substantially the same manner as the classical ELISA test, which relies on inactivated viral antigen instead of the novel antigenic peptides of the present invention. The blood serum is diluted 1:100, the reagents and immunoglobulins are the same as in the known ELISA test. Positive results are obtained by this method, for all blood samples testing positive by other methods, with a ratio of positive to negative absorbance readings reaching a high sensitivity and reliability value: 14.

The present invention comprises a new, fully synthetic, completely safe, and reliable antigenic material that is useful for the detection of HIV antibodies, particularly in an ELISA context. The present invention represents a significant advance in the art, because the dangerous virus is not used, and need not be handled either in virulent form, during preparation of the antigen, or in latent (inactivated) form, when conducting the test procedure. Similarly, the laborious, time-consuming, and expensive cell-culture, harvesting, and purification techniques are rendered unnecessary by the use of simple but HIV-specific synthetic polypeptides. In addition, the present antigenic material and method does not suffer from the inevitable tissue contaminants associated with viral antigens. Indeed, the present diagnostic method is extremely sensitive and reliable, because it employs only specific viral epitopes. As a result, the need for verification by other test methods is minimized. The method can easily be adopted for the detection of recent HIV isolates, such as LAV 2 and HTLV III (4).

The peptidic epitopes of the invention, which correspond to antigenic material of the HIV virus, are defined in Formula I, supra. The amino acid sequences of the epitopes were derived as fragments of the amino acid protein sequences determined by the genetic code of the HIV virus. The fragments were selected to include HIV-specific antigen determinants. The resulting peptides are useful primarily for diagnostic purposes, in particular for the detection of HIV antibodies in body fluids and biological substrates, such as the blood serum of persons exposed to or infected with HIV, and also for the antagonism of pathogenic HIV proteins.

The diagnostic examination procedure is similar to the standard enzyme-linked immunosorbent assay. Microwells of the kind provided with ELISA test sets, i.e., noncoated antigen-free plastic supports, are coated with an antigenic peptide of the invention. The peptide, or preferably its conjugate, is placed in solution with a suitable macromolecular vehicle, to ensure (a) proper adhesion to the test plate material (polystyrene) and (b) non-intereference with the assay. Suitable materials include caprine or bovine serum albumin, in a phosphate buffer (pH 7.0) or a carbonate buffer (pH 9.5). After incubation at 20° C. for 4 hours and 4° C. at 44 hours, the supernatant solution containing free nonabsorbed peptide is decanted and may be used again in further coating operations. The plate wells are rinsed with phosphate buffer, and unoccupied receptor sites on the plastic plate surface are blocked by filling the wells with a 3% solution of bovine serum albumin in the same buffer. After one hour of incubation at 37° C., the walls are rinsed with phosphate buffer.

Patient's sera to be examined is diluted 1:100 and is introduced to the antigenic test plates. The plates are incubated for two hours at 37° C., the wells are rinsed successively with phosphate buffer and water, and a conjugate of animal antibody to human immunoglobulin wtih horse-radish peroxidase is added. After 2 hours of incubation at 37° C., the wells are thoroughly washed to remove soluble materials, and the conjugated peroxidase is visualized by the standard immunologic color reaction, e.g. with 3,3', 5,5'-tetramethylbenzidine or o-phenylenediamine and hydrogen peroxide. Color development may require up to 30 minutes. The color intensity is measured spectrophotometrically at the wavelength prescribed for the reagent used. Thus, in the specific procedure described above, the absorbances are read at 450 or 492 nm, respectively.

The color reaction using the antigenic peptides of the invention gave an average relative absorbance of 41.6%, as compared to the positive control value taken as 100% and obtained with an antigen prepared from native biological material, i.e., live inactivated HIV. When a negative antigen-free control serum was used for comparison, the color response fluctuated at the background level of measurement.

The antigenic peptides of the invention have been shown to induce the production of monodeterminant antibodies to pathogenic HIV proteins in preliminary in vivo experiments involving several species of laboratory animals and to induce the production of monoclonal antibodies in hybridoma cells. Animals may be immunized using a peptide of the invention or a mixture thereof, either freely or preferably by incorporation into an appropriate carrier by means of a bifunctional polycondensing agent, such as peptides polycondensed with glutaraldehyde or attached to serum bovine albumin, thyreoglobulin or limpet keyhole hemocyanin, e.g. using N,N'-dicyclohexylcarbodiimide. Freund complete adjuvants (with inactivated Koch bacilli) or muramyldipeptide was used as immunoadjuvants.

The antigenic peptides of the invention can detect the presence of HIV antibodies in in vitro diagnostic tests, and have been shown to trigger an in vivo immune response in animals.

The invention is further described according to a number of examples. It will be understood by skilled practitioners that these examples are illustrative and do not serve to limit the scope of the disclosure or the claims.

EXAMPLE 1

H-Val-Tyr-Tyr-Arg-Asp-Ser-Arg-Asn-Pro-Leu-OH

A peptide synthesizer vessel is charged with 2.5 g of a chloromethylated polystyrene resin crosslinked with 1% of divinylbenzene and esterified with leucyl-t-butyloxycarbonyl having a Leu content of 0.6 mmole per gram of resin. The synthesis included 9 reaction cycles each consisting of the following steps:

(1) removing protecting groups with trifluoroacetic acid-dichloromethane 1:1, 1×5 and 1×30 min.;
(2) washing with dichloromethane, 3×1 min.;
(3) washing with 2-propanol, 2×1 min.;
(4) washing with dichloromethane, 2×1 min.;
(5) neutralizing with triethylamine-dichloromethane 1:9, 1×1 min and 1×3 min.;
(6) washing with dichloromethane, 6×1 min.;
(7) condensation, unless otherwise stated, using preformed symmetric anhydrides (300% molar excess) until there is a negative reaction for amino groups; and
(8) washing with dichloromethane, 3×1 min.

In the course of 9 of these reaction cycles, the following protected amino acid residues were successively attached:

(a) prolyl-t-butyloxycarbonyl;
(b) asparaginyl-t-butyloxycarbonyl (condensation was performed using preformed N-hydroxybenzotriazole esters, 300% molar excess);
(c) arginyl-t-butyloxycarbonyl (p-toluenesulfonyl), by mixing the amino acid derivative with N,N'-dicyclohexylcarbodiimide as a condensing agent in the reaction vessel;
(d) seryl-t-butyloxycarbonyl (benzyl);
(e) aspartyl-t-butyloxycarbonyl (O-benzyl);
(f) arginyl-t-butyloxycarbonyl (p-toluenesulfonyl), by mixing the amino acid derivative with N,N'-dicyclohexylcarbodiimide as a condensing agent in the reaction vessel;
(g) tyrosyl-t-butyloxycarbonyl (benzyloxycarbonyl);
(h) tyrosyl-t-butyloxycarbonyl (benzyloxycarbonyl); and
(i) valyl-t-butyloxycarbonyl.

Upon completion of the synthesis, 4.1 g of the peptidyl resin was obtained. A 0.5 g sample of this material was suspended in a mixture of 0.75 ml trifluoromethanesulfonic acid, 2.5 ml of trifluoroacetic acid, and 1 ml of thioanisole. After 1 hour of stirring at ambient temperature, the product is precipitated with 100 ml of anhydrous ether, separated, washed with the same solvent, extracted with 1M acetic acid and purified on a polyacrylamide gel column (1×100 cm) using 1M acetic acid as the mobile phase, with a flow rate of 7 ml/hr. Fractions containing a homogeneous product are combined and freeze-dried. The resulting peptide material, in a yield of 113 mg, has an amino acid analysis consistent with the theoretical composition of the title polypeptide chain.

Purity was verified by analytical high performance liquid chromatography ($R_t$ 7.9 in MeOH 40%–0.1% aqueous trifluoroacetic acid solution 60%), thin-layer chromatography, and paper electrophoresis at pH 2.5.

$R_f$ 0.45 (n-butanol:acetic acid:water, 4:1:1).

Analogous procedures using appropriate amino acid derivatives provided the following peptides:

H-Val-Val-Pro-Arg-Arg-Lys-Ala-Lys-Ile-OH $R_t$ 6.8 (MeOH 45%–0.1% aqueous trifluoroacetic acid solution 55%).

$R_f$ 0.15 (BuOH:AcOH:water, 4:1:1).

H-Val-Phe-Ile-His-Asn-Phe-Lys-Arg-Lys-Gly-OH $R_t$ 6.1 (MeOH 35%–0.1% aqueous trifluoroacetic acid solution 65%).

$R_f$ 0.22 (BuOH:AcOH:water, 4:1:1).

EXAMPLE 2

H-Val-Leu-His-Thr-Gly-Glu-Arg-Asp-Trp-His-Leu-Gly-NH$_2$

A peptide synthesizer vessel is charged with 1.5 g of a benzhydrylamine-containing polystyrene resin crosslinked with 1% of divinylbenzene with an amino group content of 0.7 mmoles per gram of resin. The synthesis included 12 reaction cycles each consisting of the same steps as set forth in Example 1, with the exception that step 4 and the condensations were performed using a 300% molar excess of the corresponding N-hydroxybenzotriazole esters.

In the course of peptide synthesis, the following protected amino acid residues were successively attached, cycle by cycle:

(a) glycyl-t-butyloxycarbonyl;
(b) leucyl-t-butyloxycarbonyl;
(c) histidyl-t-butyloxycarbonyl (t-butyloxycarbonyl);
(d) triptofyl-t-butyloxycarbonyl (formyl);
(e) aspartyl-t-butyloxycarbonyl (O-benzyl);
(f) arginyl-t-butyloxycarbonyl (p-toluenesulfonyl), by mixing the amino acid derivative with N,N'-dicyclohexylcarbodiimide as a condensing agent in the reaction vessel;
(g) glutamyl-t-butyloxycarbonyl (O-benzyl);
(h) glycyl-t-butyloxycarbonyl;
(i) threonyl-t-butyloxycarbonyl (benzyl);
(j) histidyl-t-butyloxycarbonyl (t-butyloxycarbonyl);
(k) leucyl-t-butyloxycarbonyl and
(l) valyl-t-butyloxycarbonyl.

Upon completion of the synthesis, 3.1 g of the peptidyl resin was obtained. A 0.5 g sample of this material was cleaved for one hour at 0° C. using 10 ml of a 10% solution of p-thiocresol in liquid HF. In this manner, the peptide chain is separated from the resin and the protecting groups are simultaneously removed. The product is purified by high performance liquid chromatography on a silica gel column (2×50 cm) coated with hydrophobic aliphatic chains as the stationary phase and using a 0.1% trifluoroacetic acid solution in 25% aqueous methanol. Fractions containing a homogeneous product are combined and freeze-dried. The resulting peptide material, in a yield of 72 mg, has an amino acid analysis consistent with the theoretical composition of the title polypeptide chain.

Purity was verified by analytical high performance liquid chromatography ($R_t$ 8.2 in MeOH 40%–0.1% aqueous trifluoroacetic acid solution 60%), thin-layer chromatography, and paper electrophoresis at pH 2.5.

$R_f$ 0.40 (n-butanol:acetic acid:water, 4:1:1).

Analogous procedures using appropriate amino acid derivatives provided the following peptides:

H-Val-Ser-Gly-Lys-Ala-Arg-Gly-Trp-Phe-NH$_2$ $R_t$ 7.1 (MeOH 40%–0.1% aqueous trifluoroacetic acid solution 60%).

$R_f$ 0.50 (BuOH:AcOH:water, 4:1:1).

H-Val-Ser-Ile-Glu-Trp-Arg-Lys-Lys-Arg-Tyr-Ser-NH$_2$ $R_t$ 5.7 (MeOH 35%–0.1% aqueous trifluoroacetic acid solution 65%).

$R_f$ 0.47 (BuOH:AcOH:water, 4:1:1).

Typical results of the modified ELISA test for HIV antibodies, using the antigenic peptides of the invention with negative sera (NS) and patients' sera (SP1 to SP3) positive, as verified by the Western blot Method, are set forth in Table I. The test sera was diluted 1:100 and the color intensity reaction was measured on a flow photometer at two wavelengths. Positive sera commercially available from Abbott, Wellcome, Sorino, and Pasteur (SPA, SPW, SPS, and SPP, respectively) were used as controls.

TABLE I

| SERUM | NS | SP1 | SP2 | SP3 | SPA | SPW | SPS | SPP |
|---|---|---|---|---|---|---|---|---|
| ABSORBANCE (Optical density, O.D.) | 0.005 | 1.19 | 1.43 | 1.43 | 1.8 | 1.02 | 1.08 | 1.04 |

In addition, 11 more positive sera verified by the Western blot Method for the presence of antibodies were evaluated. At the same dilution ratio of 1 to 100, the absorbance readings ranged from 0.6 to 1.7. Simultaneously measured negative control sera gave absorbance O.D. values of less than 0.1.

To assay possible nonspecific positive responses, 50 serum samples from patients with lymphoma or related tumorous diseases were analyzed. The sera was diluted 1 to 10 and 1 to 50, and the tests were always performed in triplicate. The absorbance O.D. readings obtained did not exceed 0.1, with the exception of only two samples at the 1:10 dilution, in which a weak nonspecific positive reaction with an O.D. at approximately 0.2 was observed.

We claim:

1. Antigenic peptides that react with antibodies to human immunodeficiency virus (HIV) and can induce the formation of specific antibodies, such peptides having the formula H-Val-X-Y wherein X is a peptide residue selected from the group consisting of:
  Val-Pro-Arg-Arg-Lys-Ala-Lys-Ile;
  Ser-Gly-Lys-Ala-Arg-Gly-Trp-Phe;
  Tyr-Tyr-Arg-Asp-Ser-Arg-Asn-Pro-Leu;
  Phe-Ile-His-Asn-Phe-Lys-Arg-Lys-Gly;
  Ser-Ile-Glu-Trp-Arg-Lys-Lys-Arg-Tyr-Ser; and
  Leu-His-Thr-Gly-Glu-Arg-Asp-Trp-His-Leu-Gly,
and Y is selected from the group consisting of a hydroxyl residue and an amino residue.

2. An antigenic peptide that reacts with antibodies to human immunodeficiency virus (HIV) and can induce the formation of specific antibodies of the formula, H-Val-Val-Pro-Arg-Arg-Lys-Ala-Lys-Ile-OH.

3. An antigenic peptide that reacts with antibodies to human immunodeficiency virus (HIV) and can induce the formation of specific antibodies of the formula, H-Val-Ser-Gly-Lys-Ala-Arg-Gly-Trp-Phe-NH$_2$.

4. An antigenic peptide that reacts with antibodies to human immunodeficiency virus (HIV) and can induce the formation of specific antibodies of the formula, H-Val-Tyr-Tyr-Arg-Asp-Ser-Arg-Asn-Pro-Leu-OH.

5. An antigenic peptide that reacts with antibodies to human immunodeficiency virus (HIV) and can induce the formation of specific antibodies of the formula H-Val-Phe-Ile-His-Asn-Phe-Lys-Arg-Lys-Gly-OH.

6. An antigenic peptide that rects with antibodies to human immunodeficiency virus (HIV) and can induce the formation of specific antibodies of the formula H-Val-Ser-Ile-Glu-Trp-Arg-Lys-Lys-Arg-Tyr-Ser-NH$_2$.

7. An antigenic peptide that reacts with antibodies to human immunodeficiency virus (HIV) and can induce the formation of specific antibodies of the formula H-Val-Leu-His-Thr-Gly-Glu-Arg-Asp-Trp-His-Leu-Gly-NH$_2$.

8. A method of detecting antibodies specific for human immunodeficiency virus comprising the steps of contacting blood sera with an antigenic peptide that reacts with antibodies to human immunodeficiency virus (HIV) and can induce the formation of specific antibodies, such peptide having the formula H-Val-X-Y wherein X is a peptide residue is selected from the group consisting of:
  Val-Pro-Arg-Arg-Lys-Ala-Lys-Ile;
  Ser-Gly-Lys-Ala-Arg-Gly-Trp-Phe;
  Tyr-Tyr-Arg-Asp-Ser-Arg-Asn-Pro-Leu;
  Phe-Ile-His-Asn-Phe-Lys-Arg-Lys-Gly;
  Ser-Ile-Glu-Trp-Arg-Lys-Lys-Arg-Tyr-Ser; and
  Leu-His-Thr-Gly-Glu-Arg-Asp-Trp-His-Leu-Gly,
and Y is selected from the group consisting of a hydroxyl residue and an amino residue, and
  measuring the formation of antibody-antigenic peptide complexes.

9. A method of detecting antibodies specific for human immunodeficiency virus, according to claim 8, wherein the formation of antibody-antigenic peptide complexes is measured by an enayme labeled antibody.

10. A method of detecting antibodies specific for human immunodeficiency virus comprising the steps of adhesively coating the microwells of antigen-free plastic support plates with a peptide solution consisting of dissolving in buffered solution with a suitable macromolecular vehicle at least one peptide prepared according to the formula H-Val-X-Y wherein X is a polypeptide residue is selected from the group consisting of:

Val-Pro-Arg-Arg-Lys-Ala-Lys-Ile;
Ser-Gly-Lys-Ala-Arg-Gly-Trp-Phe;
Tyr-Tyr-Arg-Asp-Ser-Arg-Asn-Pro-Leu;
Phe-Ile-His-Asn-Phe-Lys-Arg-Lys-Gly;
Ser-Ile-Glu-Trp-Arg-Lys-Lys-Arg-Tyr-Ser; and
Leu-His-Thr-Gly-Glu-Arg-Asp-Trp-His-Leu-Gly, and Y is selected from the group consisting of a hydroxyl residue and an amino residue, incubating the coated support plates for 4 hours at 20° C. and for 44 hours at 44° C.,
removing the supernatant solution containing free nonadsorbed peptides,
rinsing the plates with a phosphate buffer solution,
blocking unoccupied receptor sites in the plastic surface of the plates by filling with a 3 percent solution of bovine serum albumin in the same phosphate buffer,
incubating the plates at 37° C.,
rinsing the plates with microwells with phosphate buffer;
contacting the plates with previously diluted sera to be examined for the presence of antibodies,
incubating for 2 hours at 37° C.,
rinsing successively with phosphate buffer and and water,
adding a conjugate of animal antibody to human immunoglobulin with a peroxidase,
incubating for 2 hours at 37° C.,
washing the plates, and
measuring the conjugated perioxidase color reaction spectrophotometrically after a waiting time of up to 30 minutes with a reagent selected from the group consisting of 3,3′, 5,5′-tetramethylbenzidine and o-phenylenediamine, with hydrogen peroxide.

11. A method of detecting antibodies specific for human immunodeficiency virus, according to claim 10, wherein the macromolecular vehicle is chosen from the group consisting of caprine serum albumin and bovine serum albumin in a buffer selected from the group consisting of a pH 7.0 phosphate buffer and a pH 9.5 carbonate buffer, the test sera is diluted 1:100, and the peroxidase is horse-radish peroxidase.

12. A diagnostic kit for the detection of antibodies specific for human immunodeficiency virus comprising
a plastic support plate having microwells,
an HIV antibody reactive peptide in adhesive macromolecular vehicle, the microwells being coated with the peptide-carrier combination, and the peptide having the formula H-Val-X-Y wherein X is a peptide residue is selected from the group consisting of:
Val-Pro-Arg-Arg-Lys-Ala-Lys-Ile;
Ser-Gly-Lys-Ala-Arg-Gly-Trp-Phe;
Tyr-Tyr-Arg-Asp-Ser-Arg-Asn-Pro-Leu;
Phe-Ile-His-Asn-Phe-Lys-Arg-Lys-Gly;
Ser-Ile-Glu-Trp-Arg-Lys-Lys-Arg-Tyr-Ser; and
Leu-His-Thr-Gly-Glu-Arg-Asp-Trp-His-Leu-Gly,
and Y is selected from the group consisting of a hydroxyl residue and an amino residue.

13. A diagnostic kit according to claim 12 wherein the plate is of polystyrene, the adhesive macromolecular vehicle is caprine serum albumin or bovine serum albumin, buffered with a solution chosen from the group consisting of a pH 7.0 phosphate buffer and a 9.5 pH carbonate buffer, and wherein the polypeptide-carrier-plate combination comprising the diagnostic substrate is incubated at 20° C. and then at 40° C., rinsed with phosphate buffer, treated with a 3% solution of bovine serum albumin, incubated at 37° C., and rinsed with phosphate buffer prior to use.

* * * * *

Notice of Adverse Decisions in Interference

In Interference No. 102,454, involving Patent No. 4,833,072, V. Krchnak, M. Krojidlo, O. Mach, ANTIGENIC PEPTIDES AND PROCESS FOR THEIR PREPARATION, final judgment adverse to patentees was rendered July 17, 1991, as to claims 1, 4, 5, 8-13.
*(Official Gazette August 27, 1991)*